US011103536B2

(12) United States Patent
Morse et al.

(10) Patent No.: US 11,103,536 B2
(45) Date of Patent: *Aug. 31, 2021

(54) MICRONIZED PLACENTAL TISSUE COMPOSITIONS AND METHODS OF MAKING AND USING THE SAME

(71) Applicant: MiMedx Group, Inc., Marietta, GA (US)

(72) Inventors: Brenda S. Morse, Chamblee, GA (US); Somaly Sith, Stone Mountain, GA (US); Randall Spencer, Kennesaw, GA (US); Steven Ray, Kingston, GA (US); John Daniel, Kennesaw, GA (US); Robert Tofe, Denver, CO (US)

(73) Assignee: MiMedx Group, Inc., Marietta, GA (US)

(*) Notice: Subject to any disclaimer, the term of this patent is extended or adjusted under 35 U.S.C. 154(b) by 27 days.

This patent is subject to a terminal disclaimer.

(21) Appl. No.: 16/520,909

(22) Filed: Jul. 24, 2019

(65) Prior Publication Data

US 2019/0374584 A1    Dec. 12, 2019

Related U.S. Application Data

(63) Continuation of application No. 14/286,638, filed on May 23, 2014, now Pat. No. 10,376,546, which is a continuation of application No. 13/787,612, filed on Mar. 6, 2013, now Pat. No. 10,105,397, which is a continuation of application No. PCT/US2012/024798, filed on Feb. 13, 2012.

(60) Provisional application No. 61/442,346, filed on Feb. 14, 2011, provisional application No. 61/543,995, filed on Oct. 6, 2011.

(51) Int. Cl.
| A61K 35/50 | (2015.01) |
| A61K 35/12 | (2015.01) |
| A61K 8/98 | (2006.01) |
| A61L 27/36 | (2006.01) |
| A61Q 19/00 | (2006.01) |
| A61P 17/02 | (2006.01) |

(52) U.S. Cl.
CPC .............. *A61K 35/50* (2013.01); *A61K 8/982* (2013.01); *A61K 35/12* (2013.01); *A61L 27/3604* (2013.01); *A61L 27/3683* (2013.01); *A61L 27/3695* (2013.01); *A61P 17/02* (2018.01); *A61Q 19/00* (2013.01); *A61L 2400/06* (2013.01); *A61L 2430/34* (2013.01)

(58) Field of Classification Search
None
See application file for complete search history.

(56) References Cited

U.S. PATENT DOCUMENTS

| 2,694,914 | A | 11/1954 | Glover, Jr. |
| 3,272,204 | A | 9/1966 | Artandi et al. |
| 4,564,368 | A | 1/1986 | Sawyer et al. |
| 4,745,771 | A | 5/1988 | Linner et al. |
| 4,968,325 | A | 11/1990 | Black et al. |
| 5,118,867 | A | 6/1992 | Bahrmann et al. |
| 5,284,655 | A | 2/1994 | Bogdansky et al. |
| 6,030,635 | A | 2/2000 | Gertzman et al. |
| 6,387,369 | B1 | 5/2002 | Pittenger et al. |
| 6,936,271 | B1 | 9/2005 | Oliver et al. |
| 7,311,904 | B2 | 12/2007 | Hariri |
| 7,311,905 | B2 | 12/2007 | Hariri |
| 7,871,646 | B2 | 1/2011 | Ghinelli |
| 8,067,044 | B2 | 11/2011 | Henry et al. |
| 8,153,162 | B2 | 4/2012 | Tseng et al. |
| 8,323,701 | B2 | 12/2012 | Daniel et al. |
| 8,357,403 | B2 | 1/2013 | Daniel et al. |
| 8,372,439 | B2 | 2/2013 | Daniel et al. |
| 8,409,626 | B2 | 4/2013 | Daniel et al. |
| 8,623,421 | B2 | 1/2014 | Daniel |
| 8,904,664 | B2 | 12/2014 | Pringle et al. |
| 9,180,145 | B2 | 11/2015 | Brown et al. |
| 2002/0019516 | A1 | 2/2002 | Noff et al. |
| 2002/0123141 | A1 | 9/2002 | Hariri |
| 2002/0160510 | A1 | 10/2002 | Hariri |
| 2003/0032179 | A1 | 2/2003 | Hariri |
| 2003/0187515 | A1 | 10/2003 | Hariri et al. |
| 2004/0028711 | A1 | 2/2004 | Uchida et al. |
| 2004/0048796 | A1 | 3/2004 | Hariri et al. |
| 2006/0140913 | A1 | 6/2006 | Bhatia |

(Continued)

FOREIGN PATENT DOCUMENTS

| CN | 1757717 A | * | 4/2006 |
| CN | 101433556 A | | 5/2009 |

(Continued)

OTHER PUBLICATIONS

Uchide, N. et al. 2012. .Possible roles of proinflammatory and chemoattractive cytokines produced by human fetal membrane cells in the pathology of adverse pregancy outcomes associated with influenza virus infection. Mediators of Inflammation, pp. 1-32. specif . p. 7.*
EngMT. Wei, H. Preparation of dried active amnion. Chinese patent application publication No. CN1757717A; Pub. Date: Apr. 12, 2006. pp. 1-6. specif, p. 1, 2.*
O'Neil, B.A. et al. 2001. Chronic occupational repetitive strain injury. Canadian Family Physician 47: 311-316. specif. pp. 311, 312, 314.*
Diaz-Prado et al., "Potential use of the human amniotic membrane as a scaffold in human articular cartilage repair," Cell Tissue Bank, 11:183-195, (2010).

(Continued)

*Primary Examiner* — Lynn Y Fan
*Assistant Examiner* — Sharon M. Papciak
(74) *Attorney, Agent, or Firm* — Alston & Bird LLP

(57) ABSTRACT

Described herein are compositions composed of micronized placental components and pharmaceutical compositions thereof. The compositions have numerous medical applications. Methods for making and using the micronized compositions are also described herein.

8 Claims, 1 Drawing Sheet

(56) References Cited

U.S. PATENT DOCUMENTS

| | | |
|---|---|---|
| 2006/0166361 A1 | 7/2006 | Seyda et al. |
| 2006/0210532 A1 | 9/2006 | Carmeliet et al. |
| 2007/0020225 A1 | 1/2007 | Abramson et al. |
| 2007/0021762 A1* | 1/2007 | Liu .................. A61L 31/148 606/157 |
| 2007/0031471 A1 | 2/2007 | Peyman |
| 2007/0071740 A1 | 3/2007 | Tseng et al. |
| 2007/0071828 A1* | 3/2007 | Tseng ................ A61K 38/17 424/528 |
| 2007/0202189 A1 | 8/2007 | Ahlfors |
| 2007/0248575 A1 | 10/2007 | Connor et al. |
| 2007/0299043 A1 | 12/2007 | Hunter et al. |
| 2008/0046095 A1 | 2/2008 | Daniel |
| 2008/0050347 A1 | 2/2008 | Ichim |
| 2008/0069895 A1 | 3/2008 | Liu et al. |
| 2008/0131966 A1 | 6/2008 | Hariri |
| 2008/0181935 A1 | 7/2008 | Bhatia et al. |
| 2008/0181967 A1 | 7/2008 | Liu et al. |
| 2008/0193554 A1 | 8/2008 | Dua |
| 2008/0233552 A1 | 9/2008 | Ma et al. |
| 2009/0012629 A1 | 1/2009 | Yao et al. |
| 2009/0036996 A1 | 2/2009 | Roeber |
| 2009/0142831 A1 | 6/2009 | Hariri |
| 2009/0291891 A1 | 11/2009 | Neufeld |
| 2010/0028849 A1 | 2/2010 | Shelby et al. |
| 2010/0104539 A1 | 4/2010 | Daniel et al. |
| 2010/0136114 A1 | 6/2010 | Mao |
| 2010/0143312 A1 | 6/2010 | Hariri et al. |
| 2010/0178297 A1 | 7/2010 | Carmeliet et al. |
| 2010/0209408 A1 | 8/2010 | Livesey et al. |
| 2010/0260847 A1 | 10/2010 | Hariri |
| 2010/0272782 A1 | 10/2010 | Owens et al. |
| 2011/0044997 A1 | 2/2011 | Rankin et al. |
| 2011/0177150 A1 | 7/2011 | Pathak et al. |
| 2011/0189301 A1 | 8/2011 | Yang et al. |
| 2011/0206776 A1 | 8/2011 | Tom et al. |
| 2011/0307059 A1 | 12/2011 | Young et al. |
| 2012/0010708 A1 | 1/2012 | Young et al. |
| 2012/0030963 A1 | 2/2012 | Durance et al. |
| 2012/0078378 A1 | 3/2012 | Daniel et al. |
| 2012/0189583 A1 | 7/2012 | Liu et al. |
| 2012/0294910 A1 | 11/2012 | Daniel et al. |
| 2013/0218274 A1 | 8/2013 | Spencer et al. |
| 2013/0230561 A1 | 9/2013 | Daniel et al. |
| 2014/0017280 A1 | 1/2014 | Daniel et al. |
| 2014/0050788 A1 | 2/2014 | Daniel et al. |
| 2014/0051059 A1 | 2/2014 | Pringle et al. |
| 2014/0052247 A1 | 2/2014 | Daniel et al. |
| 2014/0052274 A1 | 2/2014 | Koob et al. |
| 2014/0067058 A1 | 3/2014 | Koob et al. |
| 2014/0106447 A1 | 4/2014 | Brown et al. |
| 2014/0140964 A1 | 5/2014 | Brown et al. |
| 2014/0255496 A1 | 9/2014 | Daniel et al. |
| 2014/0255508 A1 | 9/2014 | Morse et al. |
| 2014/0271728 A1 | 9/2014 | Koob et al. |
| 2014/0302162 A1 | 10/2014 | Morse et al. |
| 2015/0127116 A1 | 5/2015 | Pringle et al. |
| 2015/0250829 A1 | 9/2015 | Daniel et al. |
| 2016/0030633 A1 | 2/2016 | Daniel et al. |

FOREIGN PATENT DOCUMENTS

| | | |
|---|---|---|
| EP | 431164 A1 | 6/1991 |
| EP | 0431479 A1 | 6/1991 |
| JP | 2007-106760 A | 4/2007 |
| KR | 10/1991/0011272 | 8/1991 |
| KR | 10/1991/0011727 | 8/1991 |
| KR | 2001100588 A | 11/2001 |
| WO | WO-01/08716 A1 | 2/2001 |
| WO | WO-2004/026244 A2 | 4/2004 |
| WO | WO-2005/017165 A1 | 2/2005 |
| WO | WO-2007/010305 A1 | 1/2007 |
| WO | WO-2009/033160 A1 | 3/2009 |
| WO | WO-2009033160 A1 * | 3/2009 ............. A61K 35/19 |
| WO | WO-2009/048908 A1 | 4/2009 |
| WO | WO-2009/132186 A1 | 10/2009 |
| WO | WO-2010/029344 A2 | 3/2010 |
| WO | WO-2011/103470 | 8/2011 |
| WO | WO-2012/003377 A2 | 1/2012 |
| WO | WO-2012/112410 A2 | 8/2012 |
| WO | WO-2012/112417 A2 | 8/2012 |
| WO | WO 2012/112441 A1 | 8/2012 |
| WO | WO-2012/170905 A1 | 12/2012 |
| WO | WO-2013/095830 A1 | 6/2013 |
| WO | WO 2014/028327 A1 | 2/2014 |
| WO | WO-2014/028328 A1 | 2/2014 |

OTHER PUBLICATIONS

Niknejad et al., "Properties of the amniotic membrane for potential use in tissue engineering," European Cells and Materials, 15:88-99, (2008).

O'Grady et al., "Potential commercial and economic value of bovine amniotic fluid and placental material for Australian meat processing industry," Meat & Livestock Australia Limited, pp. 1-100, (2007).

Sigma-Aldrich, Particle Size Conversion Table [online datasheet]. Merck KGaA, pp. 1-2, (2020).

Non-Final Office Action for U.S. Appl. No. 16/164,191, dated May 13, 2020.

Non-Final Office Action for U.S. Appl. No. 16/164,274, dated May 13, 2020.

"MiMedx Group Announces Launch of EpiFixTM and Hiring of Vice President, Wound Care," MiMedx Press Release (2011).

Autiero et al., "Placental growth factor and its receptor, vascular endothelial growth factor receptor-1:novel targets for stimulation of ischemic tissue revascularization and inhibition of angiogenic and inflammatory disorders," J. Thromb. Haemo., (2003), 1:1356-1370.

AzoMaterials. Particle Size—US Sieve Series and Tyler Mesh Size Equivalents. Datasheet [online]. AZoM.com, Copyright 2000-2015. Updated Jun. 11, 2013 [retrieved on Sep. 24, 2015]. Retrieved from the Internet.

Bauer, S.M., et al., "Angiogenesis, vasculogenesis, and induction of healing in chronic wounds," Vascular and Endovascular Surgery, 2005, vol. 39, pp. 293-306.

Bennett, J.P., et al., "Treatment of chronic ulceration of the legs with human amnion," Lancet 1980, vol. 1, pp. 1153-1156.

Bergstrom, S., "Surface ultrastructure of human amnion and chorion in early pregnancy: a scanning electron microscope study," Obstetrics & Gynecology, 1971, pp. 518-524, vol. 38, No. 4.

Blakytny, R., "The molecular biology of chronic wounds and delayed healing in diabetics," Diabetic Medicine, A Journal of the British Diabetic Association 2006, vol. 23, pp. 594-608.

Borkow et al., "Reducing the risk of skin pathologies in diabetics by using copper impregnated socks," Medical Hypotheses, 2009, 1-4, doi:10.1016/j.mehy.2009.02.050.

Ennis, W., et al., "Clinical experience with a novel regenerative template for hard to heal wounds," In SAWC Annual Spring Meeting; Atlanta, GA 2012.

EpiFix Product Brochure (2009).

EpiFix Product Brochure (2011).

Extended European Search Report dated Dec. 2, 2014, for European Patent Application No. EP 12746721.

Faulk, W.P., et al., "Human amnion as an adjunct in wound healing," Lancet 1980, vol. 1, pp. 1156-1158.

Forbes, J., et al. "Dehydrated amniotic membrane allografts for the treatment of chronic wounds: a case series," Journal of Wound Care 2012, vol. 21, pp. 290, 292, 294-296.

Gruss, J.S., et al., "Human amniotic membrane: a versatile wound dressing," Canadian Medical Association Journal 1978, vol. 118, pp. 1237-1246.

Hannallah et al., "Cerebrospinal fluid leaks following cervical spine surgery," J. Bone Joint Surg. Am., (2008), 90(5):1101-1105.

Hattori et al., "Placental growth factor reconstitutes hematopoiesis by recruiting VEGFR1+ stem cells from bone-marrow microenvironment," Nat. Med., (2002), 8(8):841-849.

(56) References Cited

OTHER PUBLICATIONS

International Preliminary Report of Patentability for PCT Application No. PCT/US14/28975 dated Feb. 6, 2015.
Khan et al., "Postoperative management protocol for incidental dural tears during degenerative lumbar spine surgery: A review of 3,183 consecutive degenerative lumbar cases," Spine (Phila Pa 1976), (2006), 31(22):2609-2613.
Kim et al., "Wharton's Jelly-Derived Mesenchymal Stem Cells: Phenotypic Characterization and Optimizing Their Therapeutic Potential for Clinical Applications", 2013, Int. J. Mol. Sci., 14, pp. 1169211712, specifically p. 11694.
Koob et al., "Biological properties of dehydrated human amnionchorion composite graft: implications for chronic wound healing", International Wound Healing, 2013, 10(5):493-500.
Mardovin et al., "The Super Expansion Graft", J Burn Care Rehabil, Sep./Oct. 1992, pp. 556-559 vol. 13, No. 5.
Mayfield et al., "Watertight closure of spinal dura mater: Technical note," J. Neurosurg., (1975), 43(5):639-640.
Mermet, I., et al., Use of amniotic membrane transplantation in the treatment of venous leg ulcers. Wound repair and regeneration : official publication of the Wound Healing Society [and] the European Tissue Repair Society 2007, 15:459-464.
MiMedx Press Release, "MiMedx Scientific Study is Electronically Published in the International Wound Journal", 2013.
MiMedx: "PURION Processed Dehydrated Human Amnion/Chorion Membrane Allografts Introduction", Jul. 2012.
Nagaya et al., "Transplantation of mesenchymal stem cells improves cardiac function in a rat model of dilated cardiomyopathy", Circulation, 2005, 112(8),1128-1135.
Parolini et al., "Toward cell therapy using placenta-derived cells: disease mechanisms, cell biology, preclinical studies, and regulatory aspects at the round table", Stem Cells and Development, 2010, 19(2):143-154.
Patent Examination Report for AU Patent Application No. 2012217975 dated May 8, 2015.
PCT International Preliminary Report of Patentability for PCT Application No. PCT/US2013/054320 dated Feb. 17, 2015.
PCT International Preliminary Report of Patentability for PCT Patent Application PCT/US2013/064146, dated Sep. 25, 2014.
PCT International Preliminary Report on Patentability dated Feb. 14, 2013 for PCT Patent Application No. PCT/US2012/024814.
PCT International Preliminary Report on Patentability dated Jan. 16, 2014 in related PCT Patent Aplication No. PCT/US12/66862.
PCT International Preliminary Report on Patentability for PCT Application No. PCT/US2012/024798, dated Feb. 1, 2013.
PCT International Search Report and Written Opinion dated Dec. 29, 2014 for PCT Patent Application PCT/US2014/053270.
PCT International Search Report and Written Opinion dated Dec. 30, 2014 in PCT Patent Application No. PCT/US2014/054603.
PCT International Search Report and Written Opinion dated Jul. 24, 2014 for PCT Patent Application No. PCT/US2014/028975.
PCT International Search Report and Written Opinion for PCT Application No. PCT/US2013/054322, dated Oct. 22, 2013.
PCT International Search Report and Written Opinion for PCT Application No. PCT/US2012/066862, dated Feb. 12, 2013.
PCT International Search Report and Written Opinion for PCT Application No. PCT/US2013/054319, dated Nov. 13, 2013.
PCT International Search Report and Written Opinion for PCT Application No. PCT/US2013/054320, dated Nov. 6, 2013.
PCT International Search Report and Written Opinion for PCT Application No. PCT/US2013/054325, dated Oct. 28, 2013.
PCT International Search Report and Written Opinion for PCT Application No. PCT/US2013/055003, dated Nov. 19, 2013.
PCT International Search Report and Written Opinion for PCT Appl. PCT/US2013/064146, dated Jan. 9, 2014.
PCT International Search Report and Written Opinion for PCT Appl. PCT/US2014/012141, dated May 20, 2014.
PCT International Search Report for PCT Application No. PCT/US2012/024798, dated Jun. 20, 2012.
PCT International Search Report: and Written Opinion for PCT Appl. PCT/US13/63736, dated Aug. 12, 2014.
PROXY Biomedical, "Vitamesh", http://proxybiomedical.comilmages/ML005-01-Rev002.pdf (accessed on Jun. 5, 2014.)
Rasenack, N. et al., "Micron-size drug particles: common and novel micronization techniques", Pharmaceutical Development and Technology, 2004, 9(1): 1-13.
Serena, T, et al., "Clinical Research: Dehydrated human amniotic membrane dHAM) treatment of lower extremity venous ulceration (CR23)." In SAWC Annual Spring Meeting; Atlanta, GA. 2012.
Sheikh, E. S., et al., "Use of dehydrated human amniotic membrane allografts to promote healing in patients with refractory non healing wounds" International Wound Journal (2014), 11:711-717.
Smiell, J.M., et al., "Efficacy and safety of becaplermin (recombinant human platelet-derived growth factor-BB) in patients with nonhealing, lower extremity diabetic ulcers: a combined analysis of four randomized studies." Wound repair and regeneration : official publication of the Wound Healing Society [and] the European Tissue Repair Society 1999, 7:335-346.
Stedman's Online Dictionary. Bursa. Datasheet [online]. Lippincott Williams & Wilkins Copyright 2009 [retrieved on Sep. 24, 2015]. Retrieved from the internet: <URL: http://www.azom.com/article.aspx?ArticleD=1417>p. 2.
Steed, D.L., et al. Amnion-derived cellular cytokine solution: a physiological combination of cytokines for wound healing. Eplasty 2008, 8:e18.
Subrahmanyam, M., "Amniotic membrane as a cover for microskin grafts." British journal of plastic surgery 1995, 48:477-478.
Tao, et al., "Implantation of amniotic membrane to reduce postlaminectomy epidural adhesions," Eur. Spine. J., (2009), 18:1202-1212.
The Engineering ToolBox, Particle Sizes. Datasheet [online]. [retrieved on Oct. 28, 2015]. Retrieved from the Internet: <URL: http(s)://www.engineering.toolbox.com/particle-sizes-d_934.html> pp. 1-5. specif. pp. 1,2.
Thomson Database WPI XP002732611 entry concerning KR 2001-0100588, dated Nov. 14, 2001—Abstract.
Turk, M., et al., 2002, "Micronization of pharmaceutical substances by the Rapid Expansion of Supercritical Solutions (RESS): a promising method to improve bioavailability of poorly soluble pharmaceutical agnets," Journal of Supercritical Fluids 22:75-84, specifically p. 75.
Uchide, N. et al., 2012, "Possible roles of proinflammatory and chemoattractive cytokines produced by human fetal membrane cells in the pathology of adverse pregnancy outcomes associated with influenza virus infection", Mediators of Inflammation 2012: 1-32. specif. p. 7.
Ueta, M., "Immunosuppressive properties of human amniotic membrane for mixed lymphocyte reaction." Clinical and experimental immunology 2002, 129:464-470.
U.S. Appl. No. 13/719,148.
U.S. Appl. No. 13/744,331.
U.S. Appl. No. 13/745,642.
U.S. Appl. No. 13/983,301.
Werner, S. et al. "Regulation of wound healing by growth factors and cytokines." Physiological reviews 2003, 83:835-870.
Wieman, T.J., et al.,"Efficacy and safety of a topical gel formulation of recombinant human platelet-derived growth factor-BB (becaplermin) in patients with chronic neuropathic diabetic ulcers. A phase III randomized placebo-controlled double-blind study." Diabetes care 1998, 21:822-827.
Zelen, C.M., et al. "A prospective randomised comparative parallel study of amniotic membrane wound graft in the management of diabetic foot ulcers." International wound journal 2013, 10:502-507.
Office Action for Korean Application No. 10-2013-7023726 dated Dec. 20, 2018.
Office Action for European Application No. 17190524.3 dated Jan. 25, 2019, 4 pages.

\* cited by examiner

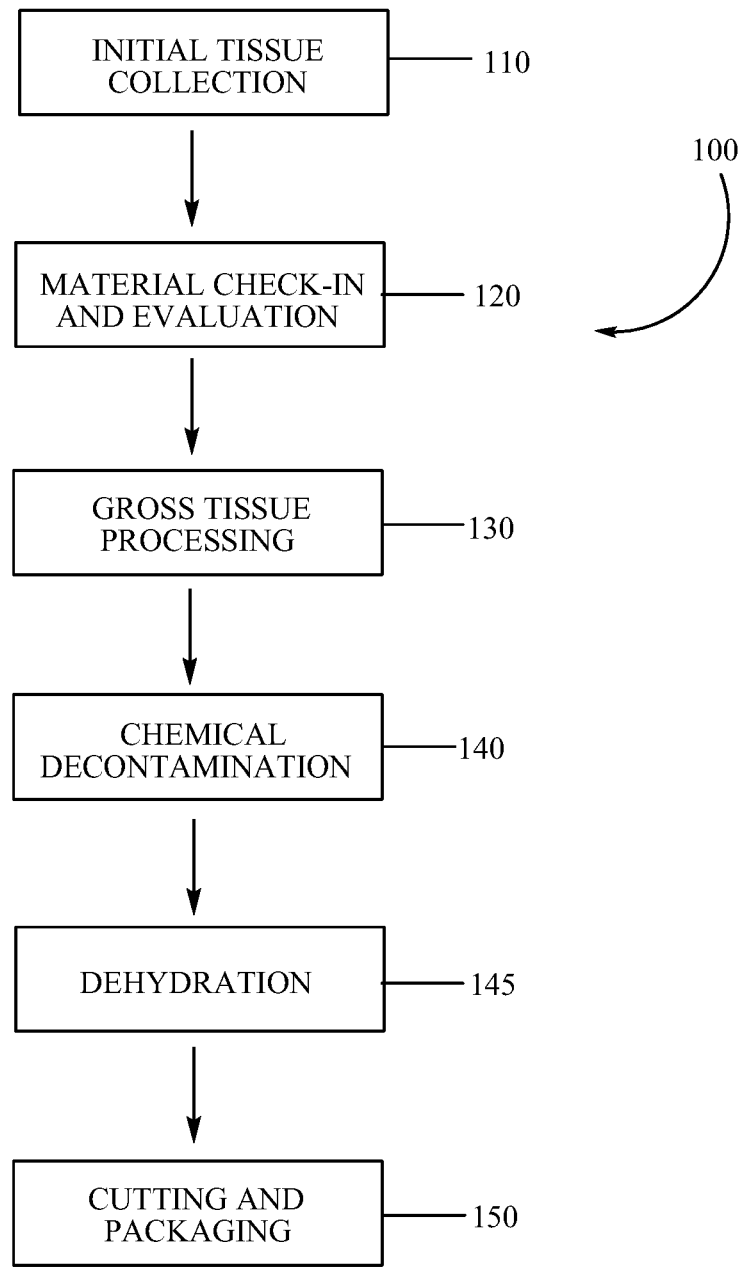

MICRONIZED PLACENTAL TISSUE COMPOSITIONS AND METHODS OF MAKING AND USING THE SAME

CROSS REFERENCE TO RELATED APPLICATIONS

This application is a continuation of U.S. patent application Ser. No. 14/286,638, filed May 23, 2014 (allowed), which is a continuation of U.S. patent application Ser. No. 13/787,612, filed Oct. 23, 2018 (now U.S. Pat. No. 10,105, 397), which is a continuation of PCT International Application No. PCT/US2012/024798, filed Feb. 13, 2012, which claims priority upon U.S. provisional application Ser. No. 61/442,346, filed Feb. 14, 2011, and Ser. No. 61/543,995, filed Oct. 6, 2011. These applications are hereby incorporated by reference in their entireties for all of their teachings.

BACKGROUND

Placental tissue is typically harvested after an elective Cesarean surgery. The placenta is composed of the umbilical cord and amniotic sac. The amniotic sac, commonly referred to as the amniotic membrane, has two primary layers of tissue, amnion and chorion. Amnion tissue is the innermost layer of the amniotic sac and in direct contact with the amniotic fluid. The amniotic sac contains the amniotic fluid and protects the fetal environment. Histological evaluation indicates that the membrane layers of the amnion consist of single layer of epithelium cells, thin reticular fibers (basement membrane), a thick compact layer, and fibroblast layer. The fibrous layer of amnion (i.e., the basement membrane) contains collagen types IV, V, and VII, and cell-adhesion bio-active factors including fibronectin and laminins Described herein is unique approach to using placental tissue components in wound healing and other medical applications.

SUMMARY

Described herein are composition composed of micronized placental components and pharmaceutical compositions thereof. The compositions have numerous medical applications. Methods for making and using the micronized compositions are also described herein.

The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

FIG. 1 is an overview flow chart of the process for making the micronized compositions described herein.

DETAILED DESCRIPTION

Before the present articles and methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a bioactive agent" includes mixtures of two or more such agents, and the like.

"Optional" or "optionally" means that the subsequently described event or circumstance can or cannot occur, and that the description includes instances where the event or circumstance occurs and instances where it does not. For example, the phrase "optionally cleaning step" means that the cleaning step may or may not be performed.

The term "subject" as used herein is any vertebrate organism.

The term "amnion" as used herein includes amniotic membrane where the intermediate tissue layer is intact or has been substantially removed.

Titles or subtitles may be used in the specification for the convenience of a reader, which are not intended to influence the scope of the present invention. Additionally, some terms used in this specification are more specifically defined below.

I. Micronized Compositions and Methods for Making Thereof

Described herein are compositions composed of micronized placental components and pharmaceutical compositions thereof. In one aspect, the composition includes (a) micronized amnion, chorion, intermediate tissue layer, or any combination thereof and (b) a pharmaceutically acceptable carrier. In one aspect, the composition includes micronized amnion and intermediate tissue layer. In another aspect, the composition includes micronized amnion and chorion.

FIG. 1 depicts an overview (100) and certain aspects of the steps to harvest, process, and prepare placental material for use in the preparation of the micronized compositions described herein. More detailed descriptions and discussion regarding each individual step will follow. Initially, the placental tissue is collected from a consenting patient following an elective Cesarean surgery (step 110). The material is preserved and transported in conventional tissue preservation manner to a suitable processing location or facility for check-in and evaluation (step 120). Gross processing, handling, and separation of the tissue layers then takes place (step 130). Acceptable tissue is then decontaminated (step 140) and dehydrated (step 145). After decontamination dehydration, the placental components (e.g., amnion, intermediate tissue layer and/or chorion individually or as grafts) are then micronized (step 150). Each step is described in detail below.

Initial Tissue Collection (Step 110)

The components used to produce the micronized compositions described herein are derived from the placenta. The source of the placenta can vary. In one aspect, the placenta is derived from a mammal such as human and other animals including, but not limited to, cows, pigs, and the like can be used herein. In the case of humans, the recovery of the placenta originates in a hospital, where it is collected during a Cesarean section birth. The donor, referring to the mother who is about to give birth, voluntarily submits to a comprehensive screening process designed to provide the safest tissue possible for transplantation. The screening process preferably tests for antibodies to the human immunodeficiency virus type 1 and type 2 (anti-HIV-1 and anti-HIV-2), antibodies to the hepatitis B virus (anti-HBV) hepatitis B surface antigens (HBsAg), antibodies to the hepatitis C virus (anti-HCV), antibodies to the human T-lymphotropic virus type I and type II (anti-HTLV-I, anti-HTLV-II), CMV, and syphilis, and nucleic acid testing for human immune-deficiency virus type 1 (HIV-1) and for the hepatitis C virus (HCV), using conventional serological tests. The above list of tests is exemplary only, as more, fewer, or different tests may be desired or necessary over time or based upon the intended use of the grafts, as will be appreciated by those skilled in the art.

Based upon a review of the donor's information and screening test results, the donor will either be deemed acceptable or not. In addition, at the time of delivery, cultures are taken to determine the presence of bacteria, for example, *Clostridium* or *Streptococcus*. If the donor's information, screening tests, and the delivery cultures are all satisfactory (i.e., do not indicate any risks or indicate acceptable level of risk), the donor is approved by a medical director and the tissue specimen is designated as initially eligible for further processing and evaluation.

Human placentas that meet the above selection criteria are preferably bagged in a saline solution in a sterile shipment bag and stored in a container of wet ice for shipment to a processing location or laboratory for further processing.

If the placenta is collected prior to the completion of obtaining the results from the screening tests and delivery cultures, such tissue is labeled and kept in quarantine. The placenta is approved for further processing only after the required screening assessments and delivery cultures, which declare the tissue safe for handling and use, are satisfied and obtains final approval from a medical director.

Material Check-in and Evaluation (Step 120)

Upon arrival at the processing center or laboratory, the shipment is opened and verified that the sterile shipment bag/container is still sealed and in the coolant, that the appropriate donor paperwork is present, and that the donor number on the paperwork matches the number on the sterile shipment bag containing the tissue. The sterile shipment bag containing the tissue is then stored in a refrigerator until ready for further processing.

Gross Tissue Processing (Step 130)

When the tissue is ready to be processed further, the sterile supplies necessary for processing the placental tissue further are assembled in a staging area in a controlled environment and are prepared for introduction into a controlled environment. In one aspect, the placenta is processed at room temperature. If the controlled environment is a manufacturing hood, the sterile supplies are opened and placed into the hood using conventional sterilization techniques. If the controlled environment is a clean room, the sterile supplies are opened and placed on a cart covered by a sterile drape. All the work surfaces are covered by a piece of sterile drape using conventional sterilization techniques, and the sterile supplies and the processing equipment are placed onto the sterile drape, again using conventional sterilization techniques.

Processing equipment is decontaminated according to conventional and industry-approved decontamination procedures and then introduced into the controlled environment. The equipment is strategically placed within the controlled environment to minimize the chance for the equipment to come in proximity to or is inadvertently contaminated by the tissue specimen.

Next, the placenta is removed from the sterile shipment bag and transferred aseptically to a sterile processing basin within the controlled environment. The sterile basin contains hyperisotonic saline solution (e.g., 18% NaCl) that is at room or near room temperature. The placenta is gently massaged to help separate blood clots and to allow the placental tissue to reach room temperature, which facilitates the separation of the placental components from each other (e.g., amnion membrane and chorion). After having warmed up to ambient temperature (e.g., after about 10-30 minutes), the placenta is then removed from the sterile processing basin and laid flat on a processing tray with the amnion membrane layer facing down for inspection.

The placenta is examined for discoloration, debris or other contamination, odor, and signs of damage. The size of the tissue is also noted. A determination is made, at this point, as to whether the tissue is acceptable for further processing.

The amnion and chorion are next carefully separated. In one aspect, the materials and equipment used in this procedure include a processing tray, 18% saline solution, sterile 4×4 sponges, and two sterile Nalgene jars. The placenta tissue is then closely examined to find an area (typically a corner) in which the amnion can be separated from the chorion. The amnion appears as a thin, opaque layer on the chorion.

The fibroblast layer is identified by gently contacting each side of the amnion with a piece of sterile gauze or a cotton tipped applicator. The fibroblast layer will stick to the test material. The amnion is placed into processing tray basement membrane layer down. Using a blunt instrument, a cell scraper, or sterile gauze, any residual blood is also removed. This step must be done with adequate care, again, so as not to tear the amnion. The cleaning of the amnion is complete once the amnion is smooth and opaque-white in appearance.

In certain aspects, the intermediate tissue layer, also referred to as the spongy layer, is substantially removed from the amnion in order to expose the fibroblast layer. The term "substantially removed" with respect to the amount of intermediate tissue layer removed is defined herein as removing greater than 90%, greater than 95%, or greater than 99% of the intermediate tissue layer from the amnion. This can be performed by peeling the intermediate tissue layer from the amnion. Alternatively, the intermediate tissue layer can be removed from the amnion by wiping the intermediate tissue layer with gauze or other suitable wipe. The resulting amnion can be subsequently decontaminated using the process described below.

In certain aspects, the epithelium layer present on the amnion is substantially removed in order to expose the basement layer of the amnion. The term "substantially removed" with respect to the amount of epithelium removed is defined herein as removing greater than 90%, greater than 95%, or greater than 99% of the epithelial cells from the amnion. The presence or absence of epithelial cells remaining on the amnion layer can be evaluated using techniques known in the art. For example, after removal of the epithelial cell layer, a representative tissue sample from the processing lot is placed onto a standard microscope examination slide. The tissue sample is then stained using Eosin Y Stain and evaluated as described below. The sample is then covered and allowed to stand. Once an adequate amount of time has passed to allow for staining, visual observation is done under magnification.

The epithelium layer can be removed by techniques known in the art. For example, the epithelium layer can be scraped off of the amnion using a cell scraper. Other techniques include, but are not limited to, freezing the membrane, physical removal using a cell scraper, or exposing the epithelial cells to nonionic detergents, anionic detergents, and nucleases. The de-epithelialized tissue is then evaluated to determine that the basement membrane has not been compromised and remains intact. This step is performed after completion of the processing step and the before the tissue has been dehydrated as described in the next section. For example, a representative sample graft is removed for microscopic analysis. The tissue sample is place onto a standard slide, stained with Eosin Y and viewed under the microscope. If epithelium is present, it will appear as cobblestone-shaped cells.

The methods described herein do not remove all cellular components in the amnion. This technique is referred to in the art as "decellularization." Decellularization generally involves the physical and/or chemical removal of all cells present in the amnion, which includes epithelial cells and fibroblast cells. For example, although the removal of epithelial cells is optional, the fibroblast layer present in the amnion stromal layer is intact, even if the intermediate tissue layer is removed.

Chemical Decontamination (Step 140)

The amnion and chorion isolated above can be chemically decontaminated using the techniques described below. In one aspect, the amnion and chorion is decontaminated at room temperature. In one aspect, the amnion produced in step 130 (e.g., with or without the intermediate tissue layer) can be placed into a sterile Nalgene jar for the next step. In one aspect, the following procedure can be used to clean the amnion. A Nalgene jar is aseptically filled with 18% saline hypertonic solution and sealed (or sealed with a top). The jar is then placed on a rocker platform and agitated for between 30 and 90 minutes, which further cleans the amnion of contaminants. If the rocker platform was not in the critical environment (e.g., the manufacturing hood), the Nalgene jar is returned to the controlled/sterile environment and opened. Using sterile forceps or by aseptically decanting the contents, the amnion is gently removed from the Nalgene jar containing the 18% hyperisotonic saline solution and placed into an empty Nalgene jar. This empty Nalgene jar with the amnion is then aseptically filled with a premixed antibiotic solution. In one aspect, the premixed antibiotic solution is composed of a cocktail of antibiotics, such as Streptomycin Sulfate and Gentamicin Sulfate. Other antibiotics, such as Polymixin B Sulfate and Bacitracin, or similar antibiotics now available or available in the future, are also suitable. Additionally, it is preferred that the antibiotic solution be at room temperature when added so that it does not change the temperature of or otherwise damage the amnion. This jar or container containing the amnion and antibiotics is then sealed or closed and placed on a rocker platform and agitated for, preferably, between 60 and 90 minutes. Such rocking or agitation of the amnion within the antibiotic solution further cleans the tissue of contaminants and bacteria. Optionally, the amnion can be washed with a detergent. In one aspect, the amnion can be washed with 0.1 to 10%, 0.1 to 5%, 0.1 to 1%, or 0.5% Triton-X wash solution.

If the rocker platform was not in the critical environment (e.g., the manufacturing hood), the jar or container containing the amnion and antibiotics is then returned to the critical/sterile environment and opened. Using sterile forceps, the amnion is gently removed from the jar or container and placed in a sterile basin containing sterile water or normal saline (0.9% saline solution). The amnion is allowed to soak in place in the sterile water/normal saline solution for at least 10 to 15 minutes. The amnion may be slightly agitated to facilitate removal of the antibiotic solution and any other contaminants from the tissue. After at least 10 to 15 minutes, the amnion is ready to be dehydrated and processed further.

In the case of chorion, the following exemplary procedure can be used. After separation of the chorion from the amnion and removal of clotted blood from the fibrous layer, the chorion is rinsed in 18% saline solution for 15 minutes to 60 minutes. During the first rinse cycle, 18% saline is heated in a sterile container using a laboratory heating plate such that the solution temperature is approximately 48° C. The solution is decanted, the chorion tissue is placed into the sterile container, and decanted saline solution is poured into the container. The container is sealed and placed on a rocker plate and agitated for 15 minutes to 60 minutes. After 1 hour agitation bath, the chorion tissue was removed and placed into second heated agitation bath for an additional 15 minutes to 60 minutes rinse cycle. Optionally, the chorion tissue can be washed with a detergent (e.g., Triton-X wash solution) as discussed above for the decontamination of amnion. The container is sealed and agitated without heat for 15 minutes to 120 minutes. The chorion tissue is next washed with deionized water (250 ml of DI water×4) with vigorous motion for each rinse. The tissue is removed and placed into a container of 1×PBS w/EDTA solution. The container is sealed and agitated for 1 hour at controlled temperature for 8 hours. The chorion tissue is removed and rinsed using sterile water. A visual inspection was performed to remove any remaining discolored fibrous blood material from the chorion tissue. The chorion tissue should have a cream white visual appearance with no evidence of brownish discoloration.

Dehydration (Step 145)

In one aspect, the amnion, chorion, intermediate tissue layer, or any combination thereof can be processed into tissue grafts (i.e., laminates) that are subsequently micronized. In another aspect, the individual amnion, chorion, intermediate tissue layers can be dehydrated independently and subsequently micronized alone or a s a mixture of components. In one aspect, the tissue (i.e., individual membrane or graft) is dehydrated by chemical dehydration followed by freeze-drying. In one aspect, the chemical dehydration step is performed by contacting the amnion, chorion, and/or intermediate layer with a polar organic solvent for a sufficient time and amount in order to substantially (i.e., greater than 90%, greater than 95%, or greater than 99%) or completely remove residual water present in the tissue (i.e., dehydrate the tissue). The solvent can be protic or aprotic. Examples of polar organic solvents useful herein include, but are not limited to, alcohols, ketones, ethers, aldehydes, or any combination thereof. Specific, non-limiting examples include DMSO, acetone, tetrahydrofuran, ethanol, isopropanol, or any combination thereof. In one aspect, the placental tissue is contacted with a polar organic solvent at room temperature. No additional steps are required, and the tissue can be freeze-dried directly as discussed below.

After chemical dehydration, the tissue is freeze-dried in order to remove any residual water and polar organic solvent. In one aspect, the amnion, chorion, and/or intermediate layer can be laid on a suitable drying fixture prior to freeze-drying. For example, one or more strips of amnion can be laid on a suitable drying fixture. Next, chorion is laid on top of the amnion. In this aspect, an amnion/chorion tissue graft is produced. Alternatively, a strip of amnion can be placed on a first drying fixture, and a strip of chorion can be placed on a second drying fixture. The drying fixture is preferably sized to be large enough to receive the placental tissue, fully, in laid out, flat fashion. In one aspect, the drying fixture is made of Teflon or of Delrin, which is the brand name for an acetal resin engineering plastic invented and sold by DuPont and which is also available commercially from Werner Machine, Inc. in Marietta, Ga. Any other suitable material that is heat and cut resistant, capable of being formed into an appropriate shape to receive wet tissue can also be used for the drying fixture.

Once the tissue is placed on the drying fixture, the drying fixture is placed in the freeze-dryer. The use of the freeze-dryer to dehydrate the tissue can be more efficient and thorough compared to other techniques such as thermal dehydration. In general, it is desirable to avoid ice crystal formation in the placental tissue as this may damage the extracellular matrix in the tissue. By chemically dehydrating the placental tissue prior to freeze-drying, this problem can be avoided.

In another aspect, the dehydration step involves applying heat to the tissue. In one aspect, the amnion, chorion, and/or intermediate layer is laid on a suitable drying fixture (either as individual strips or as a laminate discussed above), and the drying fixture is placed in a sterile Tyvex (or similar, breathable, heat-resistant, and sealable material) dehydration bag and sealed. The breathable dehydration bag prevents the tissue from drying too quickly. If multiple drying fixtures are being processed simultaneously, each drying fixture is either placed in its own Tyvex bag or, alternatively, placed into a suitable mounting frame that is designed to hold multiple drying frames thereon and the entire frame is then placed into a larger, single sterile Tyvex dehydration bag and sealed.

The Tyvex dehydration bag containing the one or more drying fixtures is then placed into a non-vacuum oven or incubator that has been preheated to approximately 35 to 50 degrees Celcius. The Tyvex bag remains in the oven for between 30 to 120 minutes. In one aspect, the heating step can be performed at 45 minutes at a temperature of approximately 45 degrees Celcius to dry the tissue sufficiently but without over-drying or burning the tissue. The specific temperature and time for any specific oven will need to be calibrated and adjusted based on other factors including altitude, size of the oven, accuracy of the oven temperature, material used for the drying fixture, number of drying fixtures being dried simultaneously, whether a single or multiple frames of drying fixtures are dried simultaneously, and the like.

Preparation of Micronized Compositions and Pharmaceutical Compositions Thereof (Step 150)

Once the amnion, chorion, and/or intermediate tissue layer have been dehydrated individually or in the form a of tissue graft, the dehydrated tissue(s) is micronized. The micronized compositions can be produced using instruments known in the art. For example, the Retsch Oscillating Mill MM400 can be used to produce the micronized compositions described herein. The particle size of the materials in the micronized composition can vary as well depending upon the application of the micronized composition. In one aspect, the micronized composition has particles that are less than 500 µm, less than 400 µm, less than 300 µm, or from 25 µm to 300 µm, from 25 µm to 200 µm, or from 25 µm to 150 µm. In certain aspects, particles having a larger diameter (e.g. 150 µm to 350 µm) are desirable.

In one aspect, micronization is performed by mechanical grinding or shredding. In another aspect, micronization is performed cryogenic grinding. In this aspect, the grinding jar containing the tissue is continually cooled with liquid nitrogen from the integrated cooling system before and during the grinding process. Thus the sample is embrittled and volatile components are preserved. Moreover, the denaturing of proteins in the amnion, intermediate tissue layer, and/or chorion is minimized or prevented. In one aspect, the CryoMill manufactured by Retsch can be used in this aspect.

The selection of components used to make the micronized components described herein can vary depending upon the end-use of the composition. For example, amnion, chorion, intermediate tissue layer, or any combination thereof as individual components can be admixed with one another and subsequently micronized. In another aspect, one or more tissue grafts composed of one or more amnion, chorion, intermediate tissue layers, or any combination thereof (i.e., laminates) can be micronized. In a further aspect, one or more tissue grafts composed of one or more amnion, chorion, intermediate tissue layers, or any combination can be admixed with amnion, chorion, intermediate tissue layer, or any combination thereof as individual components and subsequently micronized.

The amount of different components used to make the micronized compositions described herein can vary depending upon the application of the micronized composition. In one aspect, when the micronized composition is composed of amnion (with or without the intermediate tissue layer) and intermediate tissue layer, the weight ratio of amnion to intermediate tissue layer is from 10:1 to 1:10, 9:1 to 1:1, 8:1 to 1:1, 7:1 to 1:1, 6:1 to 1:1, 5:1 to 1:1, 4:1 to 1:1, 3:1 to 1:1, 2:1 to 1:1, or about 1:1. In another aspect, when the micronized composition is composed of amnion (with or without the intermediate tissue layer) and chorion, the weight ratio of chorion to amnion is from 10:1 to 1:10, 9:1 to 1:1, 8:1 to 1:1, 7:1 to 1:1, 6:1 to 1:1, 5:1 to 1:1, 4:1 to 1:1, 3:1 to 1:1, 2:1 to 1:1, or about 1:1.

In addition to amnion, the intermediate tissue layer, and chorion, additional components can be added to the composition prior to and/or after micronization. In one aspect, a filler can be added. Examples of fillers include, but are not limited to, allograft pericardium, allograft acellular dermis, Wharton's jelly separated from vascular structures (i.e., umbilical vein and artery) and surrounding membrane, purified xenograft Type-1 collagen, biocellulose polymers or copolymers, biocompatible synthetic polymer or copolymer films, purified small intestinal submucosa, bladder acellular matrix, cadaveric fascia, or any combination thereof.

In another aspect, a bioactive agent can be added to the composition prior to and/or after micronization. Examples of bioactive agents include, but are not limited to, naturally occurring growth factors sourced from platelet concentrates, either using autologous blood collection and separation products, or platelet concentrates sourced from expired banked blood; bone marrow aspirate; stem cells derived from concentrated human placental cord blood stem cells, concentrated amniotic fluid stem cells or stem cells grown in a bioreactor; or antibiotics. Upon application of the micronized composition with bioactive agent to the region of interest, the bioactive agent is delivered to the region over time. Thus, the micronized particles described herein are useful as delivery devices of bioactive agents and other pharmaceutical agents when administered to a subject. Release profiles can be modified based on, among other things, the selection of the components used to make the micronized compositions as well as the size of the particles.

In a further aspect, the amnion can be cross-linked with the intermediate tissue layer, chorion, or a second amnion tissue. For example, a cross-linking agent can be added to the composition (e.g., amnion, chorion, intermediate tissue layer, or any combination thereof as individual components and/or as tissue grafts) prior to and/or after micronization. In general, the cross-linking agent is nontoxic and non-immunogenic. When the amnion, intermediate tissue layer, and/or chorion (or a tissue graft thereof) are treated with the cross-linking agent, the cross-linking agent can be the same or different. In one aspect, the amnion, intermediate tissue layer, and chorion can be treated separately with a cross-linking agent or, in the alternative, the amnion, intermediate tissue layer, and chorion can be treated together with the same cross-linking agent. In certain aspects, the amnion, intermediate tissue layer, and chorion can be treated with two or more different cross-linking agents. The conditions for treating the amnion, intermediate tissue layer, and chorion can vary. In other aspects, the amnion, intermediate tissue layer, and/or chorion can be micronized, and the micronized composition can subsequently be treated with a cross-linking agent. In one aspect, the concentration of the cross-linking agent is from 0.1 M to 5 M, 0.1 M to 4 M, 0.1 M to 3 M, 0.1 M to 2 M, or 0.1 M to 1 M.

The cross-linking agent generally possesses two or more functional groups capable of reacting with proteins to produce covalent bonds. In one aspect, the cross-linking agent possesses groups that can react with amino groups present on the protein. Examples of such functional groups include, but are not limited to, hydroxyl groups, substituted or unsubstituted amino groups, carboxyl groups, and aldehyde groups. In one aspect, the cross-linker can be a dialdehyde such as, for example, glutaraldehyde. In another aspect, the cross-linker can be a carbodiimide such as, for example, (N-(3-dimethylaminopropyl)-N'-ethyl-carbodiimide (EDC). In other aspects, the cross-linker can be an oxidized dextran, p-azidobenzoyl hydrazide, N-[alpha-maleimidoacetoxy] succinimide ester, p-azidophenyl glyoxal monohydrate, bis-[beta-(4-azidosalicylamido)ethyl]disulfide, bis-[sulfosuccinimidyl]suberate, dithiobis[succinimidyl]propionate, disuccinimidyl suberate, and 1-ethyl-3-[3-dimethylaminopropyl]carbodiimide hydrochloride, a bifunctional oxirane (OXR), or ethylene glycol diglycidyl ether (EGDE).

In one aspect, sugar is the cross-linking agent, where the sugar can react with proteins present in the amnion, intermediate tissue layer, and chorion to form a covalent bond. For example, the sugar can react with proteins by the Maillard reaction, which is initiated by the nonenzymatic glycosylation of amino groups on proteins by reducing sugars and leads to the subsequent formation of covalent bonds. Examples of sugars useful as a cross-linking agent include, but are not limited to, D-ribose, glycerose, altrose, talose, ertheose, glucose, lyxose, mannose, xylose, gulose, arabinose, idose, allose, galactose, maltose, lactose, sucrose, cellibiose, gentiobiose, melibiose, turanose, trehalose, isomaltose, or any combination thereof.

In certain aspects, the micronized composition can be used to form a three-dimensional construct. For example, the micronized particles can be treated with a cross-linking agent described above then placed in a mold having specific dimensions. Alternatively, the micronized particles can be placed into the mold and subsequently treated with the cross-linking agent. In one aspect, the cross-linked particles can be manually formed into any desired shape. In other aspects, one or more adhesives can be admixed with an adhesive prior to being introduced into the mold. Examples of such adhesives include, but are not limited to, fibrin sealants, cyanoacrylates, gelatin and thrombin products, polyethylene glycol polymer, albumin, and glutaraldehyde products. Not wishing to be bound by theory, the three-dimensional construct composed of smaller micronized particles will produce a denser product capable of bearing mechanical loads. Alternatively, larger micronized particles will produce constructs that are less dense and possess compressive properties. This feature can be useful in non-load void filling, especially where it is desirable to have a product that will conform to irregular shapes. The three-dimensional constructs can include one or more bioactive agents described herein.

In other aspects, the micronized compositions described herein can be formulated in any excipient the biological system or entity can tolerate to produce pharmaceutical compositions. Examples of such excipients include, but are not limited to, water, aqueous hyaluronic acid, saline, Ringer's solution, dextrose solution, Hank's solution, and other aqueous physiologically balanced salt solutions. Nonaqueous vehicles, such as fixed oils, vegetable oils such as olive oil and sesame oil, triglycerides, propylene glycol, polyethylene glycol, and injectable organic esters such as ethyl oleate can also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosol, cresols, formalin and benzyl alcohol. In certain aspects, the pH can be modified depending upon the mode of administration. Additionally, the pharmaceutical compositions can include carriers, thickeners, diluents, preservatives, surface active agents and the like in addition to the compounds described herein.

The pharmaceutical compositions can be prepared using techniques known in the art. In one aspect, the composition is prepared by admixing a micronized composition described herein with a pharmaceutically-acceptable compound and/or carrier. The term "admixing" is defined as mixing the two components together so that there is no chemical reaction or physical interaction. The term "admixing" also includes the chemical reaction or physical interaction between the compound and the pharmaceutically-acceptable compound.

It will be appreciated that the actual preferred amounts of micronized composition in a specified case will vary according to the specific compound being utilized, the particular compositions formulated, the mode of application, and the particular situs and subject being treated. Dosages for a given host can be determined using conventional considerations, e.g. by customary comparison of the differential activities of the subject compounds and of a known agent, e.g., by means of an appropriate conventional pharmacological protocol. Physicians and formulators, skilled in the art of determining doses of pharmaceutical compounds, will have no problems determining dose according to standard recommendations (Physician's Desk Reference, Barnhart Publishing (1999).

The pharmaceutical compositions described herein can be administered in a number of ways depending on whether local or systemic treatment is desired, and on the area to be treated. In one aspect, administration can be by injection, where the micronized composition is formulated into a liquid or gel. In other aspects, the micronized composition can be formulated to be applied internally to a subject. In other aspects, the micronized composition can be applied topically (including ophthalmically, vaginally, rectally, intranasally, orally, or directly to the skin).

In one aspect, the micronized compositions can be formulated as a topical composition applied directly to the skin. Formulations for topical administration can include, emulsions, creams, aqueous solutions, oils, ointments, pastes, gels, lotions, milks, foams, suspensions and powders. In one aspect, the topical composition can include one or more surfactants and/or emulsifiers.

Surfactants (or surface-active substances) that may be present are anionic, non-ionic, cationic and/or amphoteric surfactants. Typical examples of anionic surfactants include, but are not limited to, soaps, alkylbenzenesulfonates, alkanesulfonates, olefin sulfonates, alkyl ether sulfonates, glycerol ether sulfonates, .alpha.-methyl ester sulfonates, sulfo fatty acids, alkyl sulphates, fatty alcohol ether sulphates, glycerol ether sulphates, fatty acid ether sulphates, hydroxy mixed ether sulphates, monoglyceride (ether) sulphates, fatty acid amide (ether) sulphates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids, e.g. acyl lactylates, acyl tartrates, acyl glutamates and acyl aspartates, alkyl oligoglucoside sulphates, protein fatty acid condensates (in particular wheat-based vegetable products) and alkyl (ether) phosphates. Examples of non-ionic surfactants include, but are not limited to, fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers or mixed formals, optionally partially oxidized alk(en)yl oligoglycosides or glucoronic acid derivatives, fatty acid N-alkylglucamides, protein hydrolysates (in particular wheat-based vegetable products), polyol fatty acid esters, sugar esters, sorbitan esters, polysorbates and amine oxides. Examples of amphoteric or zwitterionic surfactants include, but are not limited to, alkylbetaines, alkylamidobetaines, aminopropionates, aminoglycinates, imidazolinium-betaines and sulfobetaines.

In one aspect, the surfactant can be fatty alcohol polyglycol ether sulphates, monoglyceride sulphates, mono- and/or dialkyl sulfosuccinates, fatty acid isethionates, fatty acid sarcosinates, fatty acid taurides, fatty acid glutamates, alpha-olefinsulfonates, ether carboxylic acids, alkyl oligoglucosides, fatty acid glucamides, alkylamidobetaines, amphoacetals and/or protein fatty acid condensates.

Examples of zwitterionic surfactants include betaines, such as N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazolines having in each case 8 to 18 carbon atoms in the alkyl or acyl group, and cocoacylaminoethylhydroxyethyl-carboxymethyl glycinate.

In one aspect, the emulsifier can be a nonionogenic surfactant selected from the following: addition products of from 2 to 30 mol of ethylene oxide and/or 0 to 5 mol of propylene oxide onto linear fatty alcohols having 8 to 22 carbon atoms, onto fatty acids having 12 to 22 carbon atoms, onto alkylphenols having 8 to 15 carbon atoms in the alkyl group, and onto alkylamines having 8 to 22 carbon atoms in the alkyl radical; alkyl and/or alkenyl oligoglycosides having 8 to 22 carbon atoms in the alk(en)yl radical and the ethoxylated analogs thereof; addition products of from 1 to 15 mol of ethylene oxide onto castor oil and/or hydrogenated castor oil; addition products of from 15 to 60 mol of ethylene oxide onto castor oil and/or hydrogenated castor oil; partial esters of glycerol and/or sorbitan with unsaturated, linear or saturated, branched fatty acids having 12 to 22 carbon atoms and/or hydroxycarboxylic acids having 3 to 18 carbon atoms, and the adducts thereof with 1 to 30 mol of ethylene oxide; partial esters of polyglycerol (average degree of self-condensation 2 to 8), trimethylolpropane, pentaerythritol, sugar alcohols (e.g. sorbitol), alkyl glucosides (e.g. methyl glucoside, butyl glucoside, lauryl glucoside), and polyglucosides (e.g. cellulose) with saturated and/or unsaturated, linear or branched fatty acids having 12 to 22 carbon atoms and/or hydroxycarboxylic acids having 3 to 18 carbon atoms, and the adducts thereof with 1 to 30 mol of ethylene oxide; mixed esters of pentaerythritol, fatty acids, citric acid and fatty alcohols and/or mixed esters of fatty acids having 6 to 22 carbon atoms, methylglucose and polyols, preferably glycerol or polyglycerol, mono-, di- and trialkyl phosphates, and mono-, di- and/or tri-PEG alkyl phosphates and salts thereof; wool wax alcohols; polysiloxane-polyalkyl-polyether copolymers and corresponding derivatives; and block copolymers, e.g. polyethylene glycol-30 dipolyhydroxystearates. In one aspect, the emulsifier is a polyalkylene glycol such as, for example, polyethylene glycol or polypropylene glycol. In another aspect, the emulsifier is polyethylene glycol having a molecular weight 100 Da to 5,000 Da, 200 Da to 2,500 Da, 300 Da to 1,000 Da, 400 Da to 750 Da, 550 Da to 650 Da, or about 600 Da.

In another aspect, the emulsifier is a poloxamer. In one aspect, the poloxamer is a nonionic triblock copolymer composed of a central hydrophobic chain of polyoxypropylene (e.g., (poly(propylene oxide)) flanked by two hydrophilic chains of polyoxyethylene (e.g., poly(ethylene oxide)). In one aspect, poloxamer has the formula

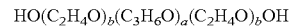

$$HO(C_2H_4O)_b(C_3H_6O)_a(C_2H_4O)_bOH$$

wherein a is from 10 to 100, 20 to 80, 25 to 70, or 25 to 70, or from 50 to 70; b is from 5 to 250, 10 to 225, 20 to 200, 50 to 200, 100 to 200, or 150 to 200. In another aspect, the poloxamer has a molecular weight from 2,000 to 15,000, 3,000 to 14,000, or 4,000 to 12,000. Poloxamers useful herein are sold under the tradename Pluronic® manufactured by BASF. Non-limiting examples of poloxamers useful herein include, but are not limited to, Pluronic® F68, P103, P105, P123, F127, and L121.

In another aspect, the emulsifier is composed of one or more fatty alcohols. In one aspect, the fatty alcohol is a liner or branched $C_6$ to $C_{35}$ fatty alcohol. Examples of fatty alcohols include, but are not limited to, capryl alcohol (1-octanol), 2-ethyl hexanol, pelargonic alcohol (1-nonanol), capric alcohol (1-decanol, decyl alcohol), undecyl alcohol (1-undecanol, undecanol, hendecanol), lauryl alcohol (dodecanol, 1-dodecanol), tridecyl alcohol (1-tridecanol, tridecanol, isotridecanol), myristyl alcohol (1-tetradecanol), pentadecyl alcohol (1-pentadecanol, pentadecanol), cetyl alcohol (1-hexadecanol), palmitoleyl alcohol (cis-9-hexadecen-1-ol), heptadecyl alcohol (1-n-heptadecanol, heptadecanol), stearyl alcohol (1-octadecanol), isostearyl alcohol (16-methylheptadecan-1-ol), elaidyl alcohol (9E-octadecen-1-ol), oleyl alcohol (cis-9-octadecen-1-ol), linoleyl alcohol (9Z, 12Z-octadecadien-1-ol), elaidolinoleyl alcohol (9E, 12E-octadecadien-1-ol), linolenyl alcohol (9Z, 12Z, 15Z-octadecatrien-1-ol) elaidolinolenyl alcohol (9E, 12E, 15-E-octadecatrien-1-ol), ricinoleyl alcohol (12-hydroxy-9-octadecen-1-ol), nonadecyl alcohol (1-nonadecanol), arachidyl alcohol (1-eicosanol), heneicosyl alcohol (1-heneicosanol), behenyl alcohol (1-docosanol), erucyl alcohol (cis-13-docosen-1-ol), lignoceryl alcohol (1-tetracosanol), ceryl alcohol (1-hexacosanol), montanyl alcohol, cluytyl alcohol (1-octacosanol), myricyl alcohol, melissyl alcohol (1-triacontanol), geddyl alcohol (1-tetratriacontanol), or cetearyl alcohol.

In one aspect, the carrier used to produce the topical composition is a mixture polyethylene and one or more fatty alcohols. For example, the carrier is composed of 50% to 99% by weight, 75% to 99% by weight, 90% to 99% by weight, or about 95% by weight polyethylene glycol and 1% to 50% by weight, 1% to 25% by weight, 1% to 10% by weight, or about 5% by weight fatty alcohol. In a further aspect, the carrier is a mixture of polyethylene glycol and cetyl alcohol.

The topical compositions can also include additional components typically present in such compositions. In one aspect, the topical composition can include one or more of the following components: fats, waxes, pearlescent waxes, bodying agents, thickeners, superfatting agents, stabilizers, polymers, silicone compounds, lecithins, phospholipids, biogenic active ingredients, deodorants, antimicrobial agents, antiperspirants, swelling agents, insect repellents, hydrotropes, solubilizers, preservatives, perfume oils and dyes. Examples of each of these components are disclosed in U.S. Pat. No. 8,067,044, which is incorporated by reference with respect these components.

The topical compositions composed of the micronized compositions described herein can be prepared by mixing the particles with the carrier for a sufficient time such that the particles are evenly dispersed throughout the carrier. In the case when the carrier is composed of two or more components, the components can be admixed with one another prior to the addition of the micronized composition. The amount of micronized composition present in the topical composition can vary depending upon the application. In one aspect, the micronized composition is from 0.5% to 20%, 1% to 10%, 2% to 5%, or about 3% by weight of the topical composition. Exemplary procedures for making topical compositions described herein are provided in the Examples.

II. Applications of Micronized Compositions

The micronized compositions described herein have numerous medical applications. In one aspect, micronized compositions composed of amnion and intermediate tissue layer can be used as dermal fillers. The skin is made up of three layers: the epidermis, dermis, and subcutaneous. The epidermis is the outer layer and functions as a barrier to the external environment. The dermis is the second layer of the skin containing the structural elements, which are collagen and elastin fibers. The collagen gives the skin its strength while the elastin fibers give the skin its elasticity. In between the epidermis and dermis is an area termed the dermal-epidermal junction. It interlocks forming fingerlike projections, called rete ridges, increasing the surface area of the epidermis that is exposed to the blood vessels in the dermis. The cells of the epidermis receive its nutrients from the blood vessels in the dermis. The last layer of skin is the subcutaneous tissue which contains the fat cells. These fat cells make the skin look plump and youthful. It also provides insulation to the body.

As a person ages, the skin goes through many changes that will eventually lead to wrinkles. The number of epidermal cells decreases causing the skin to look noticeable thinner and making it more difficult for the skin to repair itself. The dermal layer not only gets thinner, but also produces less collagen and the elastin fibers wear out causing a decrease in elasticity. These changes in the scaffolding of the skin cause the skin to wrinkle and sag. The rete-ridges of the dermal-epidermal junction flatten out, making the skin more fragile and easier for the skin to shear. The flatten rete-ridges decrease the surface area of epidermis in contact with the dermis, which leads to a decrease in the amount of nutrients available to the epidermis. This also interferes with the skin's normal repair process. In the subcutaneous layer, the fat cells get smaller with age leading to more noticeable wrinkles and sagging.

Amnion contains growth factors such as EGF, bFGF, and PDGF that promotes wound healing and re-epithelialization. Not wishing to be bound by theory, the application of a topical composition composed of the micronized compositions described herein where the epithelial layer of the skin is disrupted can be effective in delivering the growth factors directly to the injured site to promote healing. Amnion is a unique ECM due to the presence of collagen types IV, V and VII, which enables the amnion to bind water and swell.

Similarly, the intermediate tissue layer of the amniotic membrane is composed largely of glycoproteins and proteoglycans, which also enables the intermediate tissue layer to bind water. Thus, the micronized particles when applied to the skin or wound help retain water in the skin, which facilitates wound healing. For example, cell migration within the wound healing cascade is facilitated in a hydrophilic environment. The intermediate layer is also composed of collagen types I, III, and IV. Type I collagen provides mechanical strength to skin by providing a major biomechanical scaffold for cell attachment and anchorage of macromolecules. Type III collagen provides elasticity. Hence, by adding the intermediate tissue layer tissue to the deep dermis it will not only increase the elasticity and scaffolding of the skin, it may make it feel softer. Another important component in the intermediate tissue layer that is beneficial to skin is proteoglycans. As discussed above, proteoglycans allow the intermediate tissue layer to bind water to such a large degree and swell considerably. As noted before, the fat cells in the subcutaneous layer get smaller with age leading to more noticeable wrinkles. Thus, by injecting a dermal filler composed of the micronized compositions described herein can make the skin look more noticeably plump and youthful.

The selection of the carrier of the topical composition can also create a hydrophilic environment in the skin, which enhances wound healing. The size and dimension of the microparticles can also enhance dermal wound healing. For example, microparticles having a particle size of 20 μm to 100 μm, or 25 μm to 75 μm can be effective in dermal applications. Thus, in one aspect, the topical compositions described herein can help prevent or reduce wrinkle formation in a subject. In another aspect, the topical compositions can an enhance re-epithelialization of the dermal skin layer after laser-resurfacing. The topical compositions described herein can be used alone or in combination with other skin therapies such as, for example, moisturizers, Vitamin (A) creams, vitamin (E), recombinant hyaluronic acid, or human, animal, and natural oils (e.g., tee tree oil).

In other aspects, the grafts described herein can be used in orthopedic applications (i.e., sports medicine). Sports medicine includes the repair and reconstruction of various soft-tissue injuries in or around joints caused by traumas, or chronic conditions brought about by repeated motion, in active individuals and athletes. For example, sports medicine includes the treatment of a variety of different injuries associated with, but not limited to, shoulders, elbows, feet, ankles hand and wrists. In one aspect, when the micronized composition is formulated into a liquid, it can be injected into joint capsules in order to alleviate inflammation (e.g., tennis elbow, carpel tunnel, etc.). In other aspects, when the micronized composition is formulated as a gel or paste, the composition can be applied to articular surfaces in order to provide medical benefits. For example, the micronized composition can help reduce inflammation or swelling of an articular surface. In other aspects, the micronized composition can help repair and/or regrow chondrocytes. In further aspects, the micronized compositions described herein can be used in other orthopedic applications such as aid in the repair of periostium; help repair ruptured/damaged bursa; help secure void filling material during bone repair; or in applications involving a subject's extremities (e.g., anti-adhesion barrier for small bone fixation, anti-adhesion barrier where metal plating or hardware is used, or help repair ruptured/damaged bursa).

In one aspect, the micronized compositions described herein are useful in enhancing or improving wound healing. The types of wounds that present themselves to physicians on a daily bases are diverse. Acute wounds are caused by surgical intervention, trauma and burns. Chronic wounds are wounds that are delayed in closing compared to healing in an otherwise healthy individual. Examples of chronic wound types plaguing patients include diabetic foot ulcers, venous leg ulcers, pressure ulcers, arterial ulcers, and surgical wounds that become infected.

The physician's goal when treating traumatic wounds is to heal the wound while allowing the patient to retain natural function in the area of the wound with minimal scaring and infection. If a wound becomes infected, it can lead to a loss of limb or life. For the most part, physicians heal these patients without incident. However, physicians dealing with chronic wounds are mainly concerned with closing the wound as quickly as possible to minimize the risk of an infection that could lead to loss of limb or life. Chronic wounds are wounds on patients that have comorbidities that complicate or delay the healing cascade. In one aspect, the micronized compositions described herein can function as a tissue regeneration template that delivers essential wound healing factors, extracellular matrix proteins and inflammatory mediators to help reduce inflammation, enhance healing, and reduces scar tissue formation.

In another aspect, the micronized compositions described herein can be used to enhance wound healing and prevent scar formation as a result of a surgical incision. In one aspect, the micronized composition can be applied to the open incision followed by suturing the incision. For example, the micronized composition can be applied directly to the open incision by sprinkling the composition within the incision or by injecting the composition into the incision using a syringe, a small bellows device, or other related device. The micronized compositions are particularly useful where large incisions are produced by a surgical procedure. An example of such a procedure involves the treatment of spinal scoliosis, which requires a significant incision along the back of the subject. In one aspect, micronized compositions composed of an amnion/chorion laminate where the epithelium layer is intact are useful in the healing of surgical incisions with minimal scarring. With respect to wound healing and the prevention of scar formation, the micronized compositions described herein can be used in combination with other wound healing products. For example, any of the tissue grafts described herein that are a precursor to the micronized compositions can be applied to the wound after the micronized composition has been applied.

In another aspect, the micronized compositions described herein are useful for addressing or alleviating complications to the spine and surrounding regions that occur after surgery. Acute and chronic spinal injuries and pain can be attributed to trauma and/or degenerative changes in the spinal column. For the degenerative patient, there is usually a progression of possible surgeries depending on the patient's symptoms and disease state. The first surgical option when conservative therapy has failed is a laminectomy or micro-discectomy. These minimally invasive procedures are intended to relieve the pain generator or stenosis of the spinal canal. If there is progression of the disease, then other surgeries may be necessary including, but not limited to, a spinal fusion. Spinal fusions may be achieved through several approaches: anterior (from the front through the abdomen), posterior (from the back), or lateral (through the side). Each approach has advantages and disadvantages. The goal is typically to remove the spinal disc, restore disc height and fuse the two spinal vertebrae together to limit motion and further degradation. There are also surgical options for the surgeon and patient to replace the spinal disc with an artificial disc. Spine trauma is typically treated by fusing the spine levels or if a vertebrae is crushed, the surgeon may choose to do a corpectomy and fusing across the levels that were affected.

In one aspect, the micronized compositions described herein are useful in preventing or reducing scar formation on the spine or near the spine and sealing dural tears. Scar formation at or near the spine after surgery can be very debilitating and possibly require subsequent operations to address the symptoms as discussed above. The term "anti-adhesion" is also used in the art to refer to the prevention of scar tissue at or near the spine. In other aspects, the micronized compositions described herein can be used as a protective barrier, where the composition protects the spinal dura from post-surgical trauma from the surrounding surgical site. For example, the composition can prevent damage to the spinal dura caused by sharp edges from newly cut bone such as vertebrae. In other aspects, the micronized compositions can be used for anterior lumbar interbody fusion, posterior lumbar interbody fusion trans-lumbar interbody fusion, anterior cervical discectomy and fusion, micro discectomy, spinal dura repair, and as a dura sealant to prevent CSF leakage.

Depending upon the surgical procedure, the micronized composition can be applied directly to the spinal dura, the surrounding region of the spine to include nerve roots, or a combination thereof. Due to the unique structure of vertebrae, the micronized composition can be placed and affixed at the appropriate position in the subject. The micronized compositions can also provide proximal and distal barrier coverage where the spinal lamina has been removed for exposure to the affected area.

The micronized compositions are useful in preventing or reducing scar formation that can result from a variety of surgical procedures associated with the spine. The micronized compositions can be used after any procedure in the neck, mid-back, or lower back. Depending upon the application, the epithelium of the amnion can be substantially removed. For example, in posterior procedures such as a laminectomy or discectomy, the epithelium layer of the amnion is substantially removed. Removal of the epithelial cell layer exposes the amnion's basement membrane layer, which increases cell signaling characteristics. This up regulation response enhances cellular migration and expression of anti-inflammatory proteins, which inhibits fibrosis. The spinal dura is typically left unprotected following posterior procedures.

In other aspects, the epithelial cell layer of the amnion is not removed. For example, in anterior procedures or modified anterior procedures such as Anterior Lumbar Interbody Fusion (ALIF) and Transforaminal Interbody Fusion (TLIF), the amnion epithelium layer is not removed and remains intact. In these aspects, the micronized compositions provide additional protection to the vertebral surgical site by maintaining separation from the peritoneum, larger vessels, and abdominal musculature. The micronized composition serves as a reduced friction anatomical barrier against adhesions and scaring. For example, the micronized composition can prevent scar tissue binding major blood vessels to the spine. This is a common problem with post-spinal surgery, which requires a second surgical procedure to address this.

In other aspects, the micronized compositions formulated as a liquid, gel, or putty may be used in dental surgery to reduce inflammation related to gingivitis, periodontitis, mucositis, and peri-implantitis, treatment of periodontal intra-bony defects to regenerate new bone, periodontal ligament, and cementum, regenerate lost bone around dental implants, increase the amount of clinical attachment following osseous contouring, treatment of gingival recession, regeneration of interdental papilla, either through surgical reconstruction or by directly injecting the papilla to increase size and thickness, applied over the top of a barrier membrane or biocompatible mesh in alveolar vertical and horizontal bone augmentations, applied over the surgical site after primary closure to aid in healing, applied onto autograft, xenograft, alloplast, caderivic allograft or placental allograft soft tissue graft, either before, during, or after placement of the soft tissue graft in the treatment of gingival recession, increasing the amount of clinical attachment, gingival augmentations around teeth and dental implants, expanding the zone of keratinized tissue, thickening overlying gingival tissue in guided bone regeneration, mixed with a alloplast, xenograft, and or caderivic bone graft, either before, during, or after placement for use in the treatment of intrabony defects to regenerate new bone, periodontal ligament, and cementum, in guided bone regeneration regenerate lost bone around implants, site preservation, fenestration and dehiscence defects, primary and secondary alveolar ridge augmentations, sinus elevations, and gingival flap perforations. In applications involving dentin and pulpal tissue, reduce inflammation of pulpal tissue, treatment of endodontic lesions, pulpal regeneration, and injected into hollowed pulpal chamber prior to obturation in endodontic therapy. In applications involving oral mucosa tissue to reduce inflammation in oral lesions, the treatment of oral lesions, and applied onto autograft, xenograft, alloplast, caderivic allograft or placental allograft soft tissue graft either before, during, or after placement of the soft tissue graft to replace larger amounts of mucosal tissue lost through disease or traumatic injury.

In one aspect, the micronized compositions can be used to repair peripheral nerves. The micronized composition can be placed on a repaired nerve to prevent scar formation onto the healing nerve. The micronized composition can also provide a protective enclosed environment for the repair to progress successfully. In other aspects, the micronized compositions can be manufactured into a nerve regeneration tube to guide nerve growth in a protective environment where the nerve ends cannot be re-approximated. Here, nerves can re-attach up to a certain distance if the ends are allowed to meet freely without other soft tissue interfering. In another aspect, the micronized compositions can be used to wrap nerve bundles after prostatectomy procedures. These nerves are responsible for erectile function and possible continence. The micronized compositions can be applied on the nerves to keep them from scarring and possibly damaging the nerves.

In another aspect, the micronized compositions can be used in obstetrics and gynecological (OB/GYN) surgical procedures involving the treatment of diseases that may be related to the fertility of the female, pain caused by the reproductive system or cancer in the reproductive system. These procedures include the removal of uterine fibroids (myomectomy), removal of ovarian cysts, tubal ligations, endometriosis treatments, removal of some cancerous or non-cancerous tumors, and vaginal slings. These procedures may be completed through a transvaginal, abdominal or laproscopical approach.

The micronized compositions can be used as a patch to reduce the amount of scar tissue in the reproductive system after a surgical procedure. Scar tissue is another form of fibrous tissue and may also contribute to fertility problems. The ability to minimize the amount of scaring on the ovaries, or within the fallopian tubes may help with post-operative fertility and even pain. In another aspect, the micronized compositions can be used to reline the uterine wall after severe endometriosis treatments and increase the patient's ability to conceive. In a further aspect, the micronized compositions can be used as an anti-adhesion barrier after removal of ovarian cyst or aid in the repair of vaginal wall erosion.

In other aspects, the micronized compositions can be used in cardiac applications. Angina is severe chest pain due to ischemia (a lack of blood, thus a lack of oxygen supply) of the heart muscle, generally due to obstruction or spasm of the coronary arteries (the heart's blood vessels). Coronary artery disease, the main cause of angina, is due to atherosclerosis of the cardiac arteries. Various open cardiac and vascular surgery procedures to remove atherosclerotic clots require the repair, reconstruction and closure of the vessel, and the support of a regenerative tissue patch to close and patch the surgical defect. Heart by-pass grafts and heart defect reconstruction (as part of an open-heart surgical procedure) also can benefit from a patch or graft to provide a buttress to soft-tissue weakness, tissue replacement if there is a lack of suitable tissue, and also the potential to reduce adhesions to the heart itself. The micronized compositions described herein can be used as a patch to support the repair of vascular and cardiac defects caused by operations and complications such as carotid artery repair, coronary artery bypass grafting, congenital heart disease, heart valve repair, and vascular repair (i.e. peripheral vessels).

The micronized compositions described herein can be used in general surgery procedures. For example, general surgical procedures include procedures related to the abdominal cavity. These include the intestines, stomach, colon, liver, gallbladder, appendix, bile ducts and thyroid glands. Procedures may include hernias, polypectomy, cancer removal, surgical treatment of Crohn's and ulcerative colitis. These procedures may be done open or laparoscopically. In other aspects, the micronized compositions can be used to facilitate closure of anastomosis, an anti-adhesion barrier for anastomosis, or an anti-adhesion barrier for hernia repair.

In other aspects, the micronized compositions can be used in ENT procedures. Tympanoplasty is performed for the reconstruction of the eardrum (tympanic membrane) and/or the small bones of the middle ear. There are several options for treating a perforated eardrum. If the perforation is from recent trauma, many ear, nose and throat specialists will elect to watch and see if it heals on its own. If this does not occur or frequent re-perforation occurs in the same area, surgery may be considered. Tympanoplasty can be performed through the ear canal or through an incision behind the ear. Here, the surgeon harvests a graft from the tissues under the skin around the ear and uses it to reconstruct the eardrum. The micronized compositions described herein can be used to prevent the additional trauma associated with harvesting the patients' own tissue and save time in surgery. In other aspects, the micronized compositions can be used as a wound covering after adenoidectomy, a wound cover after tonsillectomy, or facilitate repair of the Snideridan membrane.

In other aspects, the micronized compositions described herein can be used in plastic surgery procedures. Scar revision is surgery to improve or reduce the appearance of scars. It also restores function and corrects skin changes (disfigurement) caused by an injury, wound, or previous surgery. Scar tissue forms as skin heals after an injury or surgery. The amount of scarring may be determined by the wound size, depth, and location; the person's age; heredity; and skin characteristics including skin color (pigmentation). Surgery involves excision of the scar and careful closure of the defect. In one aspect, the micronized compositions described herein can be used as a patch to aid in the healing and prevention of scars; and keloid or cancer revision/removal where careful approximation of soft-tissue edges is not achievable and scar tissue can result. Additionally, the anti-inflammatory properties of the micronized compositions can enhance healing as well.

In other aspects, the micronized compositions can be used in ophthalmological applications (e.g., on-lay grafts ocular surface repair) or urological applications (e.g., facilitate closure of the vas deferens during vasectomy reversal or facilitate closure of the vas deferens resulting from trauma).

In one aspect, the micronized compositions can be used in cranial dura repair and replacement, in the elimination of a frenum pull, the regeneration of lost patella tissue, the repair of the Schneiderian membrane in the sinus cavity, soft tissue around dental implants, vestibuloplasty, and guided tissue regeneration.

In addition to the selection of the components used to make the micronized compositions, the size of the particles can also vary depending upon their application. In certain aspects, micronized particles having a larger particle size can be used in several applications. For example, the micronized particles (e.g., micronized amnion chorion tissue graft) having a particle size from 150 µm to 350 µm can be effective in wound healing where it is desirable to reduce or prevent scar formation and enhance soft tissue healing. For example, the micronized particles can be injected directly into the wound. A variety of different wounds can be treated with the micronized particles. In one aspect, the micronized particles can be used to heal dermal wounds. The micronized particles can be administered at any depth within the dermal tissue of a subject (e.g., subcutaneous, sub-dermal, etc.). In one aspect, the micronized particles are useful in healing diabetic ulcers (e.g., foot ulcers). In other aspects, the dermal wounds can be tracking wounds (i.e., deep wounds that extend into the muscle tissue). Thus, the larger micronized particles can be administered intramuscularly as void packing materials for deep, large wounds.

The larger particles with greater surface area are also capable of absorbing more fluids relative to the smaller particles. Not wishing to be bound by theory, the larger particle size prevents or minimizes the possibility of the particles migrating from the wound site by blood or other physiological fluids. This feature can further enhance wound healing. The ability of the larger particles to absorb fluids makes the particles hemostatic agents, where the particles can facilitate clotting with blood and other physiological fluids in the wound. Thus, the larger particles can be admixed and re-hydrated with any excipient suitable for injection including, but not limited to, saline, blood, growth factor solutions, and the like.

In addition to the advantages discussed above, the ability of the larger micronized particles to absorb fluids permits them to be admixed with a variety of substances (e.g., any of the bioactive agents described herein) to produce pharmaceutical compositions with enhanced activity. For example, the larger particles can be mixed with additional hemostatic agents to enhance blood clotting at a wound. In other aspects, the larger particles can be admixed with autogeneous materials such as bone derived from the patient. Here the micronized particles can be administered directly to the periosteal interface. In other aspects, the larger micronized particles can be admixed with fibrin glues to enhance wound healing. The micronized particles can enhance the ability of the fibrin glue to form fibrin clots and enhance tissue repair. Thus, the larger particles in combination with the fibrin glue can further reduce the need of sutures typically used to close wounds.

Although the micronized compositions described herein can be applied directly to the tissue of a subject, they can also be applied to a wound dressing that can subsequently be applied to the subject. For example, the wound dressing can be gauze, a bandage or wrap, or any other suitable article capable of containing or affixing the micronized composition that can be applied directly to a subject.

In other aspects, the micronized compositions described herein can be applied to a medical device such as, for example, an implantable medical device. Implantable medical devices can be coated with one or more micronized compositions described herein to provide the device with beneficial properties when used in living tissue (e.g., enhanced wound healing and the prevention of scaring).

Examples of suitable implantable devices that can be coated with the micronized compositions described herein include, but are not limited to, coronary stents, peripheral stents, implants (e.g., dental, orthopedic, spinal), catheters, arterio-venous grafts, by-pass grafts, pacemaker and defibrillator leads, anastomotic clips, arterial closure devices, patent foramen ovale closure devices, and drug delivery balloons. The implantable device can be made of any suitable biocompatible materials, including biostable and bioabsorbable materials. Suitable biocompatible metallic materials include, but are not limited to, stainless steel, tantalum, titanium alloys (including nitinol), and cobalt alloys (including cobalt-Chromium-nickel and cobalt-chromium-tungsten alloys). Suitable nonmetallic biocompatible materials include, but are not limited to, polyamides, fluoropolymers, polyolefins (i.e. polypropylene, polyethylene etc.), nonabsorbable polyesters (i.e. polyethylene terephthalate), and bioabsorbable aliphatic polyesters (i.e. homopolymers and copolymers of lactic acid, glycolic acid, lactide, glycolide, para-dioxanone, trimethylene carbonate, epsiloncaprolactone, and the like, and combinations of these).

In other aspects, the micronized compositions described herein can be applied to wound healing devices. For example, the wound healing device can be a bandage, wrap, gauze, suture, or any other device used to treat wound. In these aspects, the micronized composition can be coated on and/or impregnated within the device. In other aspects, the wound healing device can be a membrane or graft used in wound healing applications, where the micronized composition is coated on one or more sides of the membrane or graft. For example, any of the tissue grafts described herein that are a precursor to the micronized compositions can be coated with the micronized compositions.

The micronized compositions can be applied to a medical device using any techniques known to those skilled in the art or those that may be developed for applying a coating to a medical device. Examples of suitable techniques for applying the coating to the medical device include spraying, dip coating, roll coating, spin coating, powder coating, and direct application by brush or needle. One skilled in the art will appreciate the many different techniques in powder coating. The micronized compositions can be applied directly to the surface of the implant device, or they can be applied over a primer or other coating material.

Finally, the three-dimensional constructs composed of the micronized compositions described herein have numerous applications. Depending upon the application of the construct, the construct can be tailor-made for the application. For example, if the construct is going to be used in hard bone repair or weight bearing applications, a dense construct can be produced from micronized particles described herein with a smaller particle sizes. Alternatively, if a softer or spongy construct is needed (e.g., a filling for a bony defect after the removal of a cyst), the construct can be made from micronized particles having a larger particle size. Thus, in one aspect, the constructs described herein can be used in orthopedic applications such as, for example, bone void filling, osteochondral repair, and articular surface repair. In another aspect, the constructs can be used in spine applications such as, for example, void filling as well as provide structural support. In dental applications, the constructs can be used as socket bone filler after tooth extraction. In another aspect, the constructs may be used as a block graft and fixed into place using bone tacks or screws in vertical and horizontal alveolar bone augmentations.

In other aspects, the three-dimensional constructs can be used in combination with any of the placental tissue described herein. For example, one or more placental tissues such as, for example, a layer of amnion, chorion, or a laminate of amnion and/or chorion can be affixed to construct. In this aspect, the construct can be inserted into a wound or void, where the amnion, chorion, or laminate is on the outside of the wound and holds the construct in place, much like a bandage.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Preparation of Micronized Composition

Example 1

The micronized human amniotic membrane injectable was composed of human amnion as described above and intermediate layer tissue obtained from placenta tissue originated in a hospital, where it is collected during a Cesarean section birth. The micronization of the tissue was performed using a Retsch Oscillating Mill MM400. Phosphate buffer was used as a carrier. The ratio of the injectable was 50 mg/mL. The concentration ratio was 60% (21 mg) amnion and 40% (14 mg) intermediate tissue layer with 0.70 mL of phosphate buffer. The micronized composition can be administered as a dermal filler with a 27 gauge needle in the deep dermis region. A suitable dose would be 0.5 cc to 1.0 cc of the composition described above.

Example 2

Amnion/chorion tissue grafts used here to produce the micronized particles were produced by the process described in US 2008/0046095, which is incorporated by reference in its entirety. Tissue grafts (4 cm×3 cm) and two 9.5 mm steel grinding balls were placed in 50 mL vials and the vials subsequently sealed. The vials were placed in the Cryo-block, and the Cryo-block was placed in a Cryo-rack. The Cryo-rack was placed into a liquid nitrogen holding Dewar. Tissue samples were subjected to vapor phase cooling for no more than 30-60 minutes. The Cryo-rack was removed from the Dewar, and the Cryo-block was removed from the Cryo-rack. The Cryo-block was placed into the Grinder (SPEX Sample Prep GenoGrinder 2010) and set at 1,500 rpm for 20 minutes. After 20 minutes has elapsed, the tissue is inspected to ensure micronization. If necessary, the tissue can be placed back into the Dewar for an additional 30-60 minutes, and moved to the grinder for an additional 20 minutes to ensure sufficient micronization. Once the tissue is sufficiently micronized it is sorted using a series of American Standard ASTM sieves. The sieves were placed in the following order: 355 µm, 300 µm, 250 µm, 150 µm, and 125 µm. The micronized material was transferred from the 50 mL vials to the 355 µm sieve. Each sieve was agitated individually in order to thoroughly separate the micronized particles. Once the micronized particles have been effectively separated using the sieves, the micronized particles having particle sizes of 355 µm, 300 µm, 250 µm, 150 µm, and 125 µm were collected in separate vials.

Preparation of Topical Compositions Composed of Micronized Particles

The following procedure produces a topical lotion composed of 95% polyethylene glycol (PEG) 600, 5% cetyl alcohol, and 10% water. PEG 600 was poured into a beaker and warmed to 45° C. While stirring under heat, water was added to the beaker. After thoroughly mixing for five minutes, cetyl alcohol was then added while continuing to stir under heat for five more minutes. The mixture was then allowed to cool at room temperature for five minutes.

Micronized amnion chorion produced in Example 2 above (particle size 25 µm to 75 µm) was then added to the mixture above to produce a 3% by weight lotion. The mixture was stirred constantly for three to five minutes at room temperature. The lotion was then placed into a refrigerator at 4° C. for fifteen minutes to cool. The final lotion has a heavy cream type consistency or viscosity. When applied directly to the skin, the lotion provides a slight moisturizing sheen with full uptake of amnion particulate material.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed:

1. A method for promoting wound healing, wherein the method comprises contacting a wound with a composition comprising micronized placental tissue particles, said tissue particles consisting essentially of an amnion layer and a chorion layer, wherein the chorion layer is layered directly over the amnion layer, wherein the intermediate layer has been substantially removed, wherein the amnion layer has an epithelial layer and an exposed fibroblast layer, and further wherein the wound healing is associated with an orthopedic application.

2. The method of claim 1, wherein the orthopedic application is selected from the group consisting of tendon repair, aiding in the repair of periosteum, repair of ruptured/damaged bursa, securing void filling materials during bone repair, repair of an articular surface, repair of a soft-tissue injury in or around a joint, application to an articular surface, repair and/or regrow chondrocytes, and as an anti-adhesion barrier.

3. The method of claim 2, wherein the soft-tissue injury is caused by trauma or repeated motion.

4. The method of claim 1, wherein the micronized placental tissue particles are dehydrated.

5. The method of claim 1, wherein the composition is an injectable composition.

6. The method of claim 1, wherein the micronized placental tissue particles are less than 500 µm.

7. The method of claim 6, wherein the micronized placental tissue particles are less than 300 µm.

8. The method of claim 7, wherein the micronized placental tissue particles are 25-150 µm.

* * * * *